(12) United States Patent
Black et al.

(10) Patent No.: US 8,530,702 B2
(45) Date of Patent: Sep. 10, 2013

(54) RECOVERY OF ACETOPHENONE DURING THE PRODUCTION OF PHENOL

(75) Inventors: Jesse Raymond Black, Katy, TX (US); Larry Wayne Payne, Houston, TX (US); Phillip Edward Unger, Houston, TX (US)

(73) Assignee: Shell Oil Company, Houston, TX (US)

( * ) Notice: Subject to any disclaimer, the term of this patent is extended or adjusted under 35 U.S.C. 154(b) by 207 days.

(21) Appl. No.: 12/739,278

(22) PCT Filed: Oct. 23, 2008

(86) PCT No.: PCT/US2008/080895
§ 371 (c)(1),
(2), (4) Date: Sep. 14, 2011

(87) PCT Pub. No.: WO2009/055535
PCT Pub. Date: Apr. 30, 2009

(65) Prior Publication Data
US 2012/0029239 A1    Feb. 2, 2012

Related U.S. Application Data

(60) Provisional application No. 60/982,777, filed on Oct. 26, 2007.

(51) Int. Cl.
*C07C 45/84*    (2006.01)

(52) U.S. Cl.
USPC .......................................... 568/324; 568/335

(58) Field of Classification Search
CPC ............................... C07C 45/46; C07C 45/81
USPC .................................................. 568/324, 335
See application file for complete search history.

(56) References Cited

U.S. PATENT DOCUMENTS

| 4,415,409 A | 11/1983 | Zudkevitch et al. | 203/51 |
| 5,240,568 A * | 8/1993 | Chan et al. | 203/84 |

FOREIGN PATENT DOCUMENTS

| GB | 724190 | 2/1955 |
| JP | 2004331532 | 11/2004 |
| WO | WO9305005 | 3/1993 |

* cited by examiner

*Primary Examiner* — Sikarl Witherspoon

(57) ABSTRACT

A method for producing acetophenone comprising: treating one or more alkylbenzenes comprising s-butylbenzene to produce a feed comprising phenol and acetophenone; separating a crude phenol stream from the feed under crude phenol separation conditions effective to produce a crude phenol heavies; and, separating an acetophenone stream directly from the crude phenol heavies under azeotropic distillation conditions.

5 Claims, 3 Drawing Sheets

US 8,530,702 B2

RECOVERY OF ACETOPHENONE DURING THE PRODUCTION OF PHENOL

The present application claims priority from U.S. Provisional Patent Application 60/982,777 filed 26 Oct. 2007.

FIELD OF THE INVENTION

The present application relates to a method for recovery of acetophenone during the production of phenol.

BACKGROUND OF THE INVENTION

In general, phenol is manufactured by oxidizing cumene to form cumene hydroperoxide. The cumene hydroperoxide is cleaved to produce phenol and acetone. If s-butylbenzene (SBB) is used as a feed in place of or in addition to cumene, the process produces the generally higher value ketone, methyl ethyl ketone (MEK), either alone or in combination with acetone. The process also produces acetophenone. Often, the acetophenone is discarded as waste.

JP 2004331532: A: 2004112: 5 D W2004-8 describes a method for producing refined AP from crude AP during the production of phenol from cumene. The crude AP is produced by thermally decomposing bottom liquid remaining after separation of phenol from crude phenol. The crude AP is introduced into a distillation tower which is decompressed to a bottom pressure of 13.33 kPa or below. In one embodiment, the bottom pressure is 6.6 kPa or below. The AP product is said to "satisf[y] quality requirement of acetophenone."

Cleavage of SBB-hydroperoxide produces different intermediates than cleavage of cumene hydroperoxide. Thermal decomposition of a bottom liquid also would be expected to alter the composition of the bottom liquid, perhaps even forming unwanted byproducts.

Methods are needed to recover acetophenone during phenol production without thermally decomposing the target stream.

SUMMARY OF THE INVENTION

The present invention provides a method for producing phenol and recovering an AP stream from a crude phenol bottoms without thermally decomposing the crude phenol bottoms.

In one embodiment, the invention provides a method for producing acetophenone comprising: treating one or more alkylbenzenes to produce a feed comprising phenol and acetophenone; separating a crude phenol stream from the feed under crude phenol separation conditions effective to produce a crude phenol heavies; and, separating an acetophenone stream directly from the crude phenol heavies under azeotropic distillation conditions.

In one embodiment, the one or more alkylbenzenes comprises s-butylbenzene.

In one embodiment, the crude phenol separation conditions comprise a pressure of from about 70 kPa (10 psi) to about 200 kPa (29 psi) and the azeotropic distillation conditions comprise a pressure of from about 0.1 kPa (0.75 mm Hg) to about 50 kPa (375 mm Hg).

In one embodiment, the method comprises separating a substantially pure acetophenone product stream directly from the crude phenol heavies.

DETAILED DESCRIPTION OF THE INVENTION

The application provides a method for producing phenol and recovering an AP stream from a crude phenol bottoms without thermally decomposing the crude phenol bottoms. In one embodiment, the phenol is produced from cumene. In one embodiment, the phenol is produced from SBB, either alone or in combination with cumene.

Where phenol is produced from SBB, the process is particularly useful because the amount of crude AP that is produced during oxidation of SBB is about 10 times the amount of crude AP produced when cumene is oxidized to produce phenol. Depending upon whether and how much cumene is used, the production of phenol from s-butylbenzene produces from about 5 wt. % to about 15 wt. % crude AP, based on the weight of phenol in the crude ketone column bottoms stream (described in more detail below). A large amount of energy is required to handle such a voluminous amount of crude AP.

In one embodiment, the process recovers about 95 wt. % or more of the total AP produced during the production of phenol. In one embodiment, the process recovers about 98 wt. % or more of the total AP. In one embodiment, the process recovers about 99 wt. % or more of the total AP. Acetophenone recovered using the process generally is of suitable quality for industrial use or as a feedstock for conversion to styrene, a material with more commercial value and/or uses than acetophenone.

AP-phenol azeotrope assists in separating the AP stream from the crude phenol heavies. The process has the advantage that it recovers most of the "additional phenol," or phenol which is either free in the crude phenol heavies or forms the AP-phenol azeotrope. In one embodiment, the process recovers 85 wt. % or more of the additional phenol, based on the total weight of phenol in the crude phenol heavies. In one embodiment, the method recovers 90 wt. % or more of the additional phenol. In one embodiment, the method recovers 92 wt. % or more of the additional phenol. In one embodiment, the method recovers 95 wt. % or more of the additional phenol.

The method of the present application is energy efficient and reduces the amount of waste and non-recoverable byproducts produced using SBB to produce phenol. The method also provides for recycle of energy and initial products in an environmentally friendly manner. The method is easily modifiable to enhance current and existing chemical process systems. The recovery system is easy to install without large capital expenditures.

A Phenol Production Process

Figure 1:
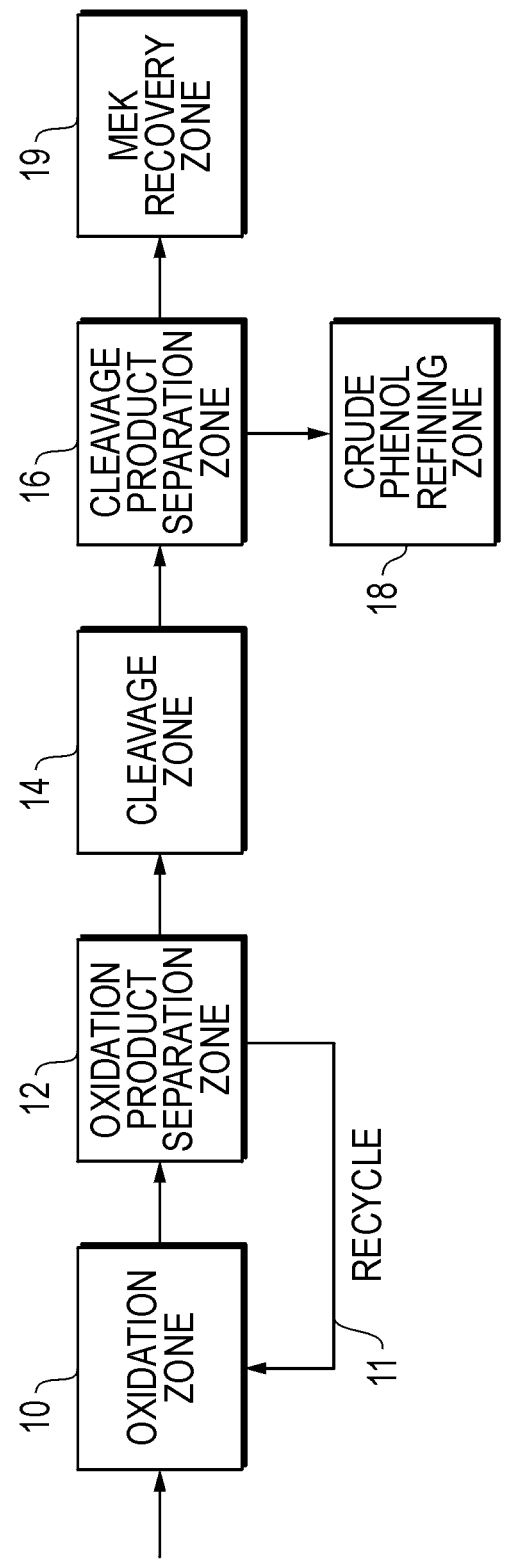
FIG. 1 is a block diagram of an exemplary phenol production process.

FIG. 1 is a block diagram of an exemplary phenol production process in which phenol, acetone, MEK, and AP are produced. The following description with reference to the Figures and to specific embodiments in the Figures is for purposes of illustration only and should not be construed as limiting the claims. The process described herein may be used during any phenol production process.

The phenol production process illustrated in FIG. 1 comprises an oxidation zone 10, an oxidation product separation zone 12, a recycle 11, a cleavage zone 14, a cleavage product separation zone 16, a crude phenol refining zone 18, and a ketone recovery zone. In one embodiment, where SBB is fed to the oxidation zone 10, the process comprises a MEK recovery zone 19, as seen in FIG. 1. The process of the present application primarily occurs in the crude phenol refining zone 18.

In the oxidation zone 10, an oxidation feed is fed to one or more oxidation reactor(s). In the oxidation reactor(s), the oxidation mixture is contacted with an oxygen-containing gas under oxidation conditions comprising an oxidation temperature effective to oxidize one or more alkylbenzenes to produce the respective hydroperoxides.

The oxidation feed comprises one or more alkylbenzenes. Suitable alkylbenzenes include, for example, cumene and/or s-butylbenzene. Where the oxidation feed comprises s-butylbenzene, the oxidation product stream comprises s-butylbenzene hydroperoxide. Where the oxidation feed comprises cumene, the oxidation product stream comprises cumene hydroperoxide.

Depending on the content of the oxidation feed, the oxidation product stream also generally comprises certain major byproducts. Major byproducts include, for example, acetophenone, di-methyl benzyl carbinol (DMBA), and ethyl methyl benzyl carbinol (EMBA). The oxidation product stream also may comprise minor by-products. Minor by-products include, for example, di-cumyl peroxide, di-s-butylperoxide, cumyl s-butyl peroxide, formic acid, acetic acid, methanol, ethanol, methyl hydroperoxide, ethyl hydroperoxide, and phenol.

In the embodiment of FIG. 1, the oxidation product is fed to an oxidation product separation zone. The oxidation product separation zone may have a variety of configurations. The oxidation product separation zone produces a cleavage reaction mixture comprising one or more alkylbenzene hydroperoxides. In one embodiment, the cleavage reaction mixture comprises sec-butylbenzene hydroperoxide and/or cumene hydroperoxide.

In the embodiment of FIG. 1, the cleavage reaction mixture is fed to a cleavage zone 14. In the cleavage zone, a majority of the hydroperoxides are cleaved. Depending upon the hydroperoxides present in the cleavage reaction mixture, the hydroperoxides are converted to phenol, MEK, and, if cumene hydroperoxide is present, acetone.

Where both s-butylbenzene and cumene have been used, and depending on the ratio of s-butylbenzene hydroperoxide to cumene hydroperoxide, the cleavage reaction produces acetone:phenol weight ratios of up to about 0.4, MEK:phenol weight ratios of from about 0.2 to 0.7, and phenol:AP weight ratios of from about 3 to 30. In an advantageous embodiment the phenol:AP ratio varies from about 8 to 12 w/w.

In FIG. 1, the cleavage product is fed to a cleavage product separation zone 16. The cleavage product separation zone 16 generally comprises a crude ketone column (CKC). In one embodiment, the crude ketone column separates the cleavage product into a crude phenol fraction and a crude ketone stream.

Where cumene is not fed to the oxidation zone, the crude ketone stream does not comprise a significant amount of acetone. In this embodiment, it may not be necessary to feed the crude ketone stream to an acetone product column (APC) before feeding the crude ketone stream to the MEK recovery zone 19. Where the cleavage product does comprise acetone, the crude ketone stream is fed to an acetone product column (APC). Acetone is recovered from the APC column as an APC overhead, and/or as an APC side draw. The APC conditions are effective to produce an APC bottoms stream comprising MEK. In one embodiment, the APC bottoms stream comprises MEK, water, hydrocarbons, condensation reaction products, sodium phenate, and combinations thereof. The APC bottoms stream is further processed to recover a MEK product in the MEK recovery zone 19.

The AP Recovery Process

The AP recovery process may comprise one or more separations. In an advantageous embodiment, the AP recovery process comprises multiple separations. In one embodiment, the AP recovery process comprises two separations. In another embodiment, the AP recovery process comprises three separations.

The various separators or "columns" may be any type of structure suitable for separating the described streams. Suitable structures include distillation columns containing internals for contacting vapor and liquid. Any type and combination of columns can be used including, for example, perforated plate columns, bubble cap columns, or packed columns. Suitable internals include, for example, trays, packing, or a combination thereof.

The Crude Phenol Separation Zone

AP Recovery Involving Three Separations

Figure 2:
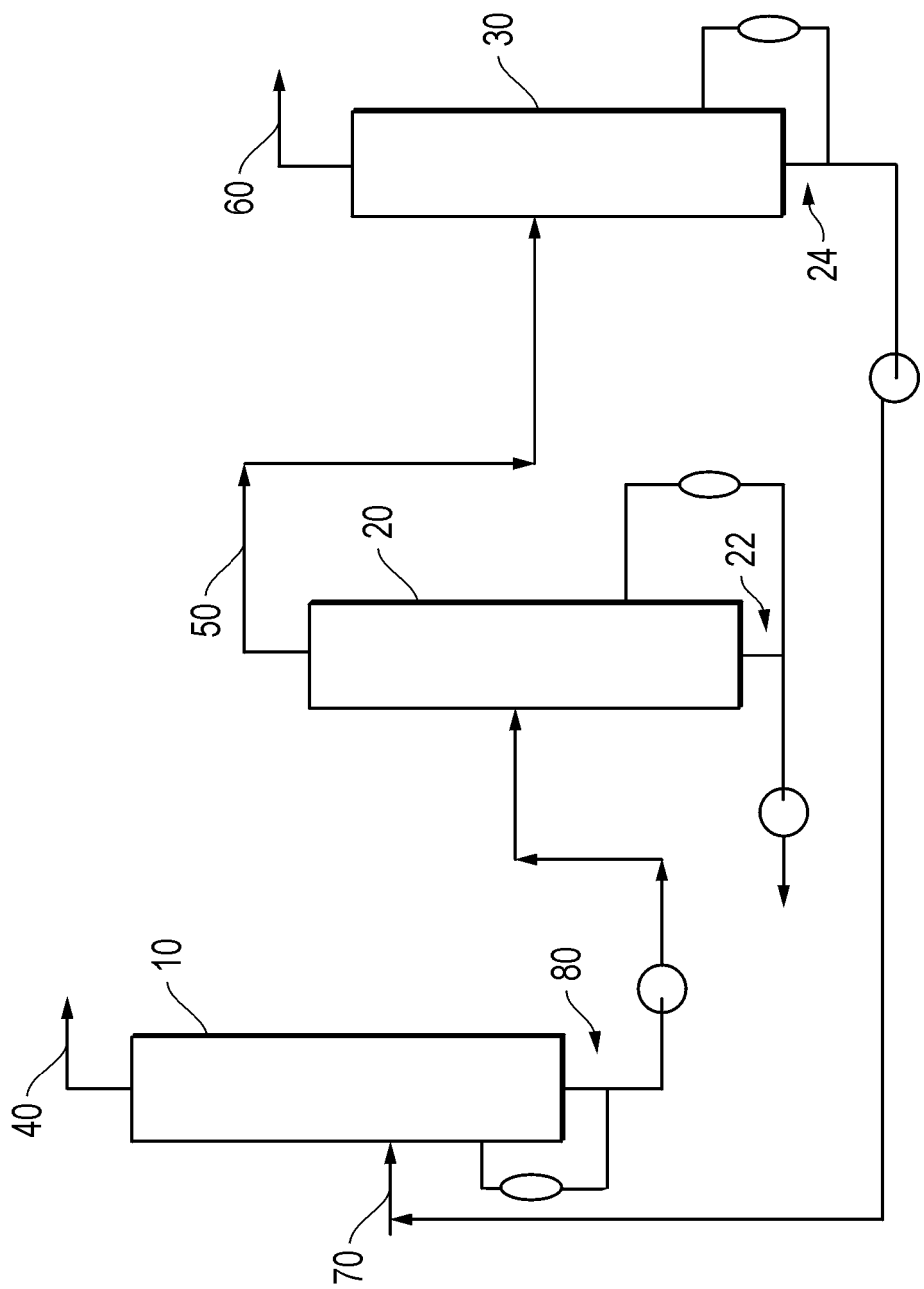
FIG. 2 is a block diagram of one embodiment of a system for performing the AP recovery process of the present application.

The following is a more detailed description of the AP recovery process comprising three separations, which is illustrated in FIG. 2.

Where the term "bottoms" is used herein, or the term "heavies," the stream generally exits the separator or column (hereafter "column") below the entry level of the feed. A "bottoms" or "heavies" may exit the column at or near the bottom of the column. For example, the stream may exit directly from the bottom of a column. The stream also may be a side cut taken near the bottom of a column. A "bottoms" or "heavies" also may comprise a combination of a stream exiting directly from the bottom and a side cut taken near the bottom of a column.

Similarly, where the term "overhead" is used, the stream generally exits a column above the entry level of the feed. An "overhead" may exit the separator or column at or near the top of a column. For example, the stream may exit directly from the top of a column. The stream also may be a side cut taken near the top of a column. An "overhead" also may be a combination of a stream exiting directly from the top and a side cut near the top of a column.

The CPC

Referring to FIG. 2, the feed 70, typically the bottoms from a crude ketone column, is fed to a crude phenol separator 10. In one embodiment, the crude phenol separator 10 is a distillation column referred to as the crude phenol column (CPC) 10. The CPC 10 has a suitable number of stages and/or packing to recover an acceptable crude phenol stream 40 from the feed 70, leaving a CPC heavies 80. In one embodiment, the CPC heavies 80 is the CPC bottoms and/or near bottoms 80.

In one embodiment, the CPC 10 is a distillation column comprising a number of theoretical stages. The number of theoretical stages may vary. As the number of stages increases, operating flexibility generally increases and variability in feed composition may be accommodated. Persons of ordinary skill in the art will be able to determine the optimum number of stages using standard procedures.

In one embodiment, the CPC 10 comprises about 10 theoretical stages or more. In one embodiment, the CPC 10 comprises about 20 theoretical stages or more. In one embodiment, the CPC 10 comprises about 60 theoretical stages or less. In one embodiment, the CPC 10 comprises about 40 theoretical stages or less.

In one embodiment, the CPC 10 also comprises a reboiler to provide heat for vapor generation and a condenser to condense vapor for generation of liquid reflux and distillate. A variety of heat sources for reboiling may be used, including steam or heat integration with other parts of the process. Heat is removed from the condenser by any suitable cooling medium. Suitable cooling mediums include cooling water, air, or heat integration with other parts of the process.

A crude phenol stream 40 is separated from the feed 70 under crude phenol separation conditions. In one embodiment, the crude phenol separation conditions are distillation conditions. The crude phenol separation conditions comprise a temperature and a pressure effective to separate the crude phenol stream 40, leaving a crude phenol heavies 80. In one embodiment, the crude phenol stream 40 undergoes additional purification using known technology.

The crude phenol heavies 80 generally comprises AP, AP-phenol azeotrope, di-methyl benzyl alcohol (DMBA), ethyl methyl benzyl alcohol (EMBA), and other higher boiling components. The crude phenol separation conditions are sufficiently mild to minimize dimerization of AP.

In one embodiment, the crude phenol separation conditions comprise a crude phenol separation pressure of about 70 kPa (10 psi) or more. In one embodiment, the crude phenol separation pressure is about 100 kPa (14 psia) or more. In one embodiment, the crude phenol separation pressure is about 200 kPa (29 psia) or less.

The crude phenol separation may be carried out at substantially any operating temperature, depending on the crude phenol separation pressure. The CPC operating temperature generally is sufficiently high to separate the crude phenol stream 40 but sufficiently low to minimize dimerization of AP. Where the operating pressure is from about 70 kPa to 200 kPa, dimerization of AP would be expected to occur at operating temperatures of about 250° C. or more. In one embodiment, the CPC operating temperature generally will be about 230° C. or less.

In one embodiment, the crude phenol stream 40 is substantially free of unwanted aromatic impurities. Unwanted aromatic impurities that may be driven into the crude phenol stream 40 by the recovery of AP include aromatic aldehydes. Unwanted aromatic aldehydes include, for example, benzaldehyde and cumene aldehyde. An acceptable crude phenol stream comprises 1 ppm or less benzaldehyde. An acceptable crude phenol stream also comprises 10 ppm or less cumene aldehyde.

The HEC

In one embodiment, an acetophenone stream 50 is separated directly from the crude phenol heavies. "Directly" means that the crude phenol heavies is not thermally decomposed before separating an acetophenone stream 50 therefrom.

In one embodiment, the crude phenol heavies 80 is fed directly to an acetophenone separator 20. In one embodiment, the acetophenone separator is a crude phenol heavy ends column (HEC) 20. In one embodiment, the crude phenol heavies 80 is fed to the HEC 20 at or near the middle of the HEC 20.

The HEC 20 is operated under HEC separation conditions effective to separate an AP stream 50 from the crude phenol heavies 80. The AP stream 50 exits the HEC 20 at the top of the HEC 20 or as a sidecut near the top of the HEC 20. The AP stream 50 comprises AP and the AP-phenol azeotrope. In one embodiment, the AP stream 50 is substantially free of unwanted aromatic impurities. Unwanted aromatic impurities that tend to fractionate with AP include, for example unwanted aromatic alcohols. Unwanted aromatic alcohols include, for example, dimethyl benzyl alcohol (DMBA) and ethyl methyl benzyl alcohol (EMBA). A substantially pure AP stream or product comprises 0.04 wt. % or less DMBA. A substantially pure AP stream or product comprises 0.01 wt. % or less EMBA. Acetophenone recovered using the process generally is of suitable quality for industrial use.

The HEC separation conditions comprise a HEC pressure and a HEC temperature effective to separate the AP stream 50 from the crude phenol heavies 80. In one embodiment, the HEC separation conditions are distillation conditions. In one embodiment, the HEC separation conditions are HEC azeotropic distillation conditions.

The HEC operating pressure is sufficiently low to cause separation of the AP stream 50 from the crude phenol heavies 80. In one embodiment, the HEC operating pressure is about 1 kPa (7.5 mm Hg) or more. In one embodiment, the HEC operating pressure is about 30 kPa (225 mm Hg) or less.

The HEC may be operated at substantially any operating temperature that is sufficiently high to separate the AP stream 50 but sufficiently low to minimize dimerization of the AP. The HEC operating temperature will vary depending upon the HEC operating pressure. At HEC operating pressures of from about 1 kPa to about 30 kPa, the HEC operating temperature generally is about 250° C. or less.

In one embodiment, the HEC 20 is a distillation column comprising a number of theoretical stages. The number of theoretical stages may vary. Persons of ordinary skill in the art will be able to determine the optimum number of stages using standard procedures.

In one embodiment, the HEC 20 comprises about 20 theoretical stages or more. In one embodiment, the HEC 20 comprises about 30 theoretical stages or more. In one embodiment, the HEC 20 comprises about 80 theoretical stages or less. In one embodiment, the HEC 10 comprises about 50 theoretical stages or less.

The HEC heavies 22 remaining after the acetophenone stream 50 is removed comprise tars and heavy ends. The HEC heavies 22 generally exit the HEC 20 at the bottom of the HEC 20 or at the near bottom of the HEC 20 as a side cut. It may be possible to identify certain components in the HEC heavies 22. However, the HEC heavies 22 generally comprise unidentified high boiling point compounds. Generally, the HEC heavies 22 is not further processed. In one embodiment, the HEC heavies is burned as fuel to provide heat for the same or for another process.

The APRC

In one embodiment, the AP stream 50 enters an AP recovery column (APRC) 30. The AP stream 50 comprises AP, AP-phenol azeotrope, and other impurities. The APRC 30 is operated under APRC azeotropic distillation conditions effective to separate a refined AP stream 60 from the crude AP stream 50. In one embodiment, the refined AP stream 60 is a substantially pure AP product.

In one embodiment, the refined AP stream 60 exits the APRC 30 as an overhead stream. In one embodiment, the refined AP stream exits the APRC at the top of the APRC 30. In one embodiment, the refined AP stream 60 exits the APRC 30 as a sidecut near the top of the APRC 30. The purity of the refined AP stream 60 will vary depending upon a number of factors. Relevant factors include, for example, the number of stages in the APRC 30, the quantity and type of packing (if any), and the azeotropic distillation conditions.

The APRC azeotropic distillation conditions generally comprise a bottoms temperature, an overhead temperature, and a top operating pressure. The APRC temperatures are sufficiently high to separate the refined AP stream 60 but sufficiently low to minimize dimerization of AP.

The AP stream 50 comprises one or more AP-phenol azeotropes. Table 1 reflects the predicted boiling points of various AP-phenol azeotropes at different pressures. As seen from Table 1, as the operating pressure of the APRC 30 is reduced, the temperature difference between the boiling point of AP and the boiling point of the various AP-phenol azeotropes increases. In other words, using a lower APRC operating pressure makes the separation easier and fewer theoretical stages will be required to accomplish the separation:

| Pressure | | Phenol BP, °F.(°C.) | AP BP, °F.(°C.) | AP-Phenol BP, °F.(°C.) | AP Mass fraction | Phenol Mass fraction |
|---|---|---|---|---|---|---|
| 50 | mmHg | 216.8 (102.7) | 239.7 (115.4) | 245.0 (118.3) | 0.707 | 0.293 |
| 100 | mmHg | 247.4 (119.7) | 273.0 (133.9) | 276.6 (135.9) | 0.725 | 0.263 |
| 5 | psia (34.5 kPa) | 295.0 (146..1) | 324.8 (182.7) | 326.4 (163.6) | 0.803 | 0.197 |
| 10 | psia (68.9 kPa) | 334.9 (168.3) | 368.4 (184.9) | 368.9 (187.2) | 0.880 | 0.120 |
| 14.7 | psia (101.3 kPa) | 359.4 (181.9) | 395.2 (201.8) | 395.3 (201.8) | 0.939 | 0.061 |
| 15.7 | psia (108.2 kPa) | 363.7 (184.3) | 400.0 (204.4) | 400.0 (204.4) | 0.950 | 0.050 |
| 19.7 | psia (135.8 kPa) | 379.2 (192.9) | 416.9 (213.8) | 416.9 (213.8) | 0.994 | 0.006 |
| 24.7 | psia (170.3 kPa) | 395.3 (201.8) | 434.7 (223.7) | | | |
| 29.7 | psia (204.8 kPa) | 409.0 (209.4) | 449.8 (232.1) | | | |
| 48.7 | psia (335.8 kPa) | 450.1 (232.3) | 495.3 (257.4) | | | |

In one embodiment, the APRC operating pressure is about 0.1 kPa or more. In one embodiment, the APRC operating pressure is about 30 kPa or less. In one embodiment, the APRC operating pressure is about 10 kPa or less. The lower limit on the APRC pressure for commercial purposes is expected to be about 1 kPa, although lower pressures such as 0.1 kPA may be possible, for example, with higher vacuum equipment and refrigerated condensing medium.

The amount of AP in the refined AP stream 60 tends to be sensitive to heat input. If excess heat is applied to the reboiler, the amount of unwanted aromatic impurities in the refined AP stream may increase. Unwanted aromatic impurities that tend to fractionate with AP include, for example unwanted aromatic alcohols. Unwanted aromatic alcohols include, for example, dimethyl benzyl alcohol (DMBA) and ethyl methyl benzyl alcohol (EMBA). In one embodiment, the refined AP stream is substantially free of unwanted aromatic impurities.

In one embodiment, where the APRC top operating pressure is from about 3 kPa to about 15 kPa, the APRC overhead temperature generally will be about 140° C. or less.

In one embodiment, the APRC azeotropic distillation conditions also comprise a mass reflux ratio of 1.8 or more, based on the reflux flow to the flow of the AP stream 50. In one embodiment, the mass reflux ratio is about 2 or more. In one embodiment, the mass reflux ratio is about 5 or less.

The number of theoretical stages may vary. Persons of ordinary skill in the art will be able to determine the optimum number of stages using standard procedures.

In one embodiment, the number of theoretical stages in the APRC is about 10 or more. In one embodiment, the number of theoretical stages in the APRC is about 20 or more. In one embodiment, the number of theoretical stages in the APRC is about 60 or less. In one embodiment, the number of theoretical stages in the APRC is about 40 or less.

Generally, the amount of AP in the refined AP stream 60 is about 95 wt. % or more, based on the total weight of the refined AP stream. In one embodiment, the amount of AP in the refined AP stream 60 is 98 wt. % or more. In one embodiment, the amount of AP in the refined AP stream is 99.9 wt. % or more.

The APRC also produces an APRC heavies 24. The APRC heavies 24 generally is the bottom stream and/or a side cut or near bottom stream of the APRC 30. The APRC heavies 24 generally comprises AP, phenol, AP-phenol azeotrope, and higher boiling impurities. In one embodiment, all or some of the APRC heavies stream 24 is recycled to the phenol production process. In one embodiment, all or some of the APRC heavies 24 is recycled to the CPC. In these embodiments, the recycled portion of the APRC heavies 24 passes through the CPC 10, the AEC 20, and the APRC 30. This permits additional phenol recovery and AP refinement and capture.

Two Separations

Figure 3:
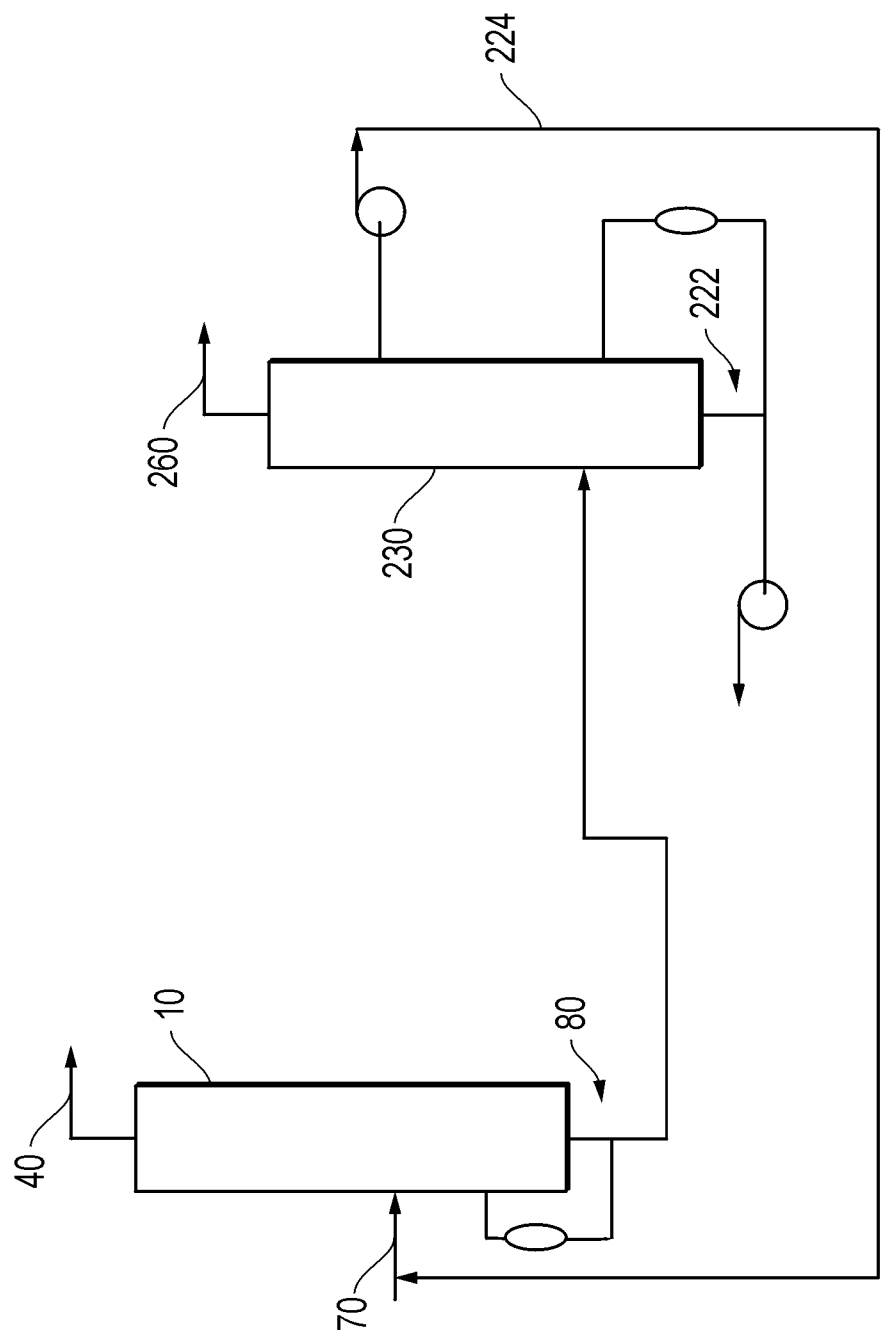
FIG. 3 is a block diagram of another embodiment of a system for performing the AP recovery process of the present application.

In another embodiment, the HEC column 20 is omitted. In this embodiment, the process comprises two separations. An exemplary illustration of this embodiment appears in FIG. 3.

In this embodiment, the crude phenol heavies 80 is fed to a "final column" 230. In one embodiment, the crude phenol heavies comprises about 3 wt. % or more phenol. In one embodiment, the crude phenol heavies 80 comprises about 10 wt. % or more phenol. In one embodiment, the crude phenol heavies 80 comprises about 30 wt. % or less phenol. In one embodiment, the crude phenol heavies 80 comprises about 15 wt % or less phenol.

The final column 230 is operated under final column azeotropic distillation conditions effective to produce: a final column overhead stream 260, a final column midstream 224, and a final column heavies 222.

Generally, the final column overhead stream 260 corresponds to the refined AP stream 60 in FIG. 2; the final column heavies 222 corresponds to the HEC heavies 22 in FIG. 2; and, the final column midstream 224 corresponds to the APRC heavies 24 in FIG. 2. In one embodiment, the final column heavies 222 are burned as fuel. In one embodiment, the final column midstream 224 is recycled back to the phenol production process. In one embodiment, the final column midstream 224 is recycled back to the CPC 10. Recycling of the final column midstream 224 to the phenol production process permits recovery of much of the phenol that was present in the crude phenol heavies 80.

The final column azeotropic distillation conditions comprise a final column bottom pressure of about 1 kPa or more. In one embodiment, the final column bottom pressure is about 6 kPa or more. In one embodiment, the final column bottom pressure is about 50 kPa or less. In one embodiment, the final column bottom pressure is about 20 kPa or less.

The final column azeotropic distillation conditions comprise a final column top pressure of about 0.1 kPa or more. In one embodiment, the final column top pressure is about 5 kPa or more. In one embodiment, the final column top pressure is about 45 kPa or less. In one embodiment, the final column top pressure is about 19 kPa or less.

The final column azeotropic distillation conditions also comprises a number of theoretical stages. The number of theoretical stages may vary. Persons of ordinary skill in the art will be able to determine the optimum number of stages using standard procedures.

In one embodiment, the azeotropic distillation conditions comprise a number of theoretical stages of about 30 or more. In one embodiment, the number of theoretical stages is about 40 or more. In one embodiment, the number of theoretical stages is about 80 or less. In one embodiment, the number of theoretical stages is about 60 or less.

In one embodiment, the AP stream is substantially free of unwanted aromatic impurities. As previously explained, unwanted aromatic impurities that tend to fractionate with AP include, for example unwanted aromatic alcohols. Unwanted aromatic alcohols include, for example, DMBA and EMBA.

The number of supply streams and exit streams to and from the various separators may vary depending upon a number of factors. For example, the number of supply and/or exit streams may vary with the composition of the feed to the oxidation process, the compositional variation of the refined AP product desired, and/or other compositional considerations.

The invention will be better understood with reference to the following examples, which are illustrative only and should not be construed as limiting.

Example 1

The crude phenol stream produced as an overhead from the CPC column during AP recovery operations was compared with the same stream produced during the last phase of a demonstration run which did not involve AP recovery.

Previously collected drummed crude phenol heavies was loaded into a mixing container, blended, and combined with a portion of recycled APRC bottoms comprising phenol rich AP-phenol azeotrope. This mixture was fed to a CPC. Crude phenol, both from any excess phenol in the crude phenol heavies as well as from breaking of the AP-phenol azeotrope, was taken overhead in the CPC and drummed for later disposal.

During normal operation of the full pilot plant the AP concentration in the crude phenol stream, taken as an overhead from the CPC, was maintained at less than 10 ppmw AP. During AP recovery the concentration of AP in the crude phenol stream ranged higher, typically in the 10-50 ppmw AP range. Some of this difference is related to the gross difference in the composition of the feed to the CPC, and the absence of the huge phenol fraction that normally traffics the upper section of the CPC and dominates the separation. During AP recovery, this flow was only a tiny fraction [0.2 lb/hr (0.1 kg/hr)–0.3 lb/hr (0.14 kg/hr)] of its normal 8+ lb/hr (3.6+ kg/hr) flow rate. This difference in column feed composition is the most likely explanation for the slightly higher AP levels seen in the crude phenol stream taken as an overhead from the CPC. It was recognized after startup of the AP recovery pilot that the feed location should have been lower in the CPC in order to compensate for the higher AP concentration of the feed.

The crude phenol heavies had a low phenol content, from about 5 wt. % to about 10 wt. % phenol, and was fed directly to the HEC. The separation performed in the HEC is nominally between AP and the HEC heavies but actually is between the AP-phenol azeotrope and the next heavier major impurity, perhaps ethyl phenyl ketone (a.k.a. propiophenone). In fact, in order to ensure minimum heavy contaminant carryover with the AP and phenol, the HEC was operated with some small net slip of AP out the bottom of the column. The net slip of AP typically was <1 wt. % of the AP concentration in the HEC bottoms stream. This small slip of AP represents a small net loss of AP, which is acceptable in order to ensure good AP product purity. The majority of the AP and phenol were taken as an overhead or near overhead from the HEC and the neat heavy ends was taken as the HEC heavies. HEC heavies were drummed for later study.

The HEC overhead comprising AP and phenol was routed to a container and from there to the APRC. The APRC had a short pasteurizing section and it was possible to take a light ends bleed and reduce light ends contamination of the side draw AP product stream. The results for certain components found in the crude phenol stream are given in the following Table:

| Component | Ratio AP to Demo | With AP Recovery average (ppmw) | Demo Run average (ppmw) |
|---|---|---|---|
| phenol | 1.0 | 94.37 | 95.72 |
| alpha-ethyl styrene | 0.3 | 61 | 187 |
| 3-phenyl-2-pentene | 0.2 | 41 | 166 |
| total sat. C5 benzenes | 6.7 | 126 | 19 |
| cis-2-phenyl-2-butene | 0.9 | 792 | 894 |
| acetic acid phenyl ester | | 35 | |
| 2-methyl benzofuran | 0.4 | 47 | 106 |
| 2-ethyl benzofuran | 2.3 | 172 | 76 |
| Unsaturated C5 benzene | 0.3 | 11 | 32 |
| acetophenone | 12.3 | 42 | 3 |

While there was some variability in the composition data, the concentrations of the trace species were all low and fairly similar. The foregoing results indicate that AP recovery did not appear to drive species to find a purge point out the top of the crude phenol column in the crude phenol stream.

Compounds lighter than phenol were found in the HEC overhead, suggesting that cracking or decomposition reactions occurred in several column sumps, presumably because of the long residence times at elevated temperatures. This was not surprising given that the electrical reboilers used in the pilot plant had order of magnitude larger internal volumes than would be true of commercial scale equipment. Also, certain heavier species, such as dimers (AMS-dimer, AMS-AES dimer 1), and certain other reactive species seem to be disappearing. It was assumed that product recoveries and purities achieved in the pilot plant may be better than those achievable at commercial scale, perhaps due to aldol condensation or other reactions occurring as a result of the longer residence times and/or higher temperatures in the pilot plant.

The top and bottoms stream flows were adjusted to force closure with the feed, and the net fresh feed composition (drummed crude phenol heavies) was not measured so the component feed rates (lb/hr) of phenol and AP were estimated from balance, forcing perfect closure. Material balance and composition data included compounds that were either possibly being formed or reacted away, or for whom material balance closure was unusually poor. However, AP and phenol showed material balance closures in line with the overall mass balance.

Based on the foregoing adjusted data, the pilot plant accomplished (a) an AP recovery of above 99 wt. %, based on the weight of net fresh feed, and (b) an additional phenol recovery of above 95 wt. %, based on the weight of net fresh feed, after material balance was determined. A commercial plant design would include two purge streams which would likely lower these recoveries. The two streams would be (a) a light ends purge from the top of the APRC, and (b) a purge from the AP-phenol azeotrope stream recycled from the bottoms of the APRC.

From the perspective of a column calibration analysis with the intent to determine an approximate number of stages, it was sufficient to consider only the key components and a reconciled overall component balance during a period of stable operation.

The APRC Column

During the three column AP pilot plant run, a side draw with a composition comprising 98.3+ wt. % AP content was produced together with an APRC bottoms with a composition comprising approximately 76 wt. % AP and 18 wt. % phenol. The reflux to feed ratio was approximately 2. The APRC was configured with 2 ft (0.6 m) of packing in the pasteurization section, 3.5 ft (1 m) of packing between the side-draw location and the feed and another 3.5 ft (1 m) of packing below the feed location. Operating pressure was 2 psia (13.8 kPa). Phenol recoveries to the bottom of the APRC in excess of 99 wt. % based on actual column feed and bottoms flows were achieved. A heavy component 2,3-dimethyl benzofuran (23DMBF) was selected as the identity of uncharacterized material. By using phenol (in the side-draw) as the heavy key and AP (in the bottoms) as the light key, a theoretical stage count of approximately 40 matched the key component concentrations using a reflux to feed ratio of 3. The calculated O'Connell overall column efficiency for this system is relatively high at 75% (due to the low relative volatility between AP and the AP/phenol azeotrope). In terms of Aspen stage nomenclature, the feed position is at stage 20 and the side draw at stage 4 (condenser=stage 1).

It was observed in the pilot plant analytical results that component alpha-methyl benzyl alcohol (AMBA) was reported to partition mostly to the ARPC bottoms whereas the Aspen model indicated that it would partition mostly to the APRC tops. As a result, there is a potential for AMBA to build up in the recycle stream comprising the APRC bottoms.

The HEC

The light key component in the HEC is phenol and the heavy key component is ethyl phenyl ketone (EPK). The HEC was piloted in the pilot plant at 2 psia (13.8 kPa) with the feed port located ⅔ of the way up the column [below top 5' (1.5 m) bed and above bottom 10' (3 m) bed].

The alternative heavy key 2-ethyl benzofuran (2EBF) could not be used since it was reported in the analytical results together with 3-phenyl-2-butanone. An unknown component with a concentration of 4-5 wt. % in the crude phenol heavies was modeled as EMBA to ensure that it partitions mostly to the HEC heavies as per pilot plant analytical results. The crude phenol heavies stream only has approximately 90% of components identified, the remainder being treated as heavy ends (TARS).

The HEC was operated at reflux rates of 10 lb/hr (4.5 kg/hr) and 15 lb/hr (6.8 kg/hr) corresponding to reflux to feed ratios of 1.5-2.3. Component balances for two operating snapshots were compiled. During this "high AP recovery" period, the column was operated with approximately 0.1-0.8 wt. % AP in the bottoms (99+ wt. % recovery to tops, based on the total weight of the HEC feed) and 50-330 ppmw EPK in the tops (1-5 wt. % recovery in tops, based on the total weight of the HEC feed).

Aspen modeling was performed to determine the number of theoretical stages estimated to match the performance of the column during these two operating snapshots. During the simulation, the feed position was maintained at the same relative position as the pilot plant column whilst the stage count was increased and the reflux rate approximately matched the plant value. In this fashion, it was determined that 36-38 theoretical stages would match plant data based on AP as the light key and EPK as the heavy key. Hence, the recommended design point for the HEC is 38 theoretical stages (excluding condenser and reboiler) with a reflux to feed ratio of 2.5.

CPC

Analysis of the CPC without AP recovery using a 2-inch (5.08 cm) I.D. perforated plate column resulted in the following design point recommendation: 50 trays, atmospheric pressure; reflux to feed ratio of 1; and, a feed location to the middle of the column.

Example 2

A three-column continuous distillation train for recovery and purification of AP was simulated as follows. In the simulation, flow rates are referenced to a feed rate to the crude phenol column of 100 lb/hr (45.4 kg/hr).

21 pounds/hr (9.5 kg/hr) of a CKC bottoms feed stream containing 10 wt. % AP and 80 wt. % phenol, based on the total weight of the CKC bottoms feed stream, and 79 pounds/hr (36 kg/hr) of a recycle stream from the bottom of the APRC containing 84 wt. % AP and 14 wt. % phenol, based on the total weight of the recycle stream, are fed to a CPC operating at a top pressure of 15.7 psia (108.2 kPa) and a bottom pressure of 20.7 psia (142.7 kPa) at a bottom temperature of 222° C. The crude phenol heavies is fed at a rate of 38 lb/hr (17 kg/hr) to a HEC operating at a top pressure of 2 psia (13.8 kPa) and a bottoms temperature of 212.2° C. 10 lb/hr (4.5 kg/hr) of HEC heavy ends containing 4% w AP and 0.3 wt. % phenol is removed from the bottom of the HEC. 28 lb/hr (12.7 kg/hr) of a crude AP stream containing 88.6 wt. % AP and 9.8 wt. % phenol, based on the total weight of the crude AP stream, is removed from the top of the HEC and fed to the APRC operating at a top pressure of 1 psia (6.9 kPa). 40 lb/hr (18.1 kg/hr) of a 98 wt. % AP stream, based on the total weight of the AP stream, is removed from the top of the APRC. 125 lb/hr (56.7 kg/hr) of the APRC bottoms containing 77 wt. % AP and 22 wt. % phenol, based on the total weight of the APRC bottoms, is recycled to the crude phenol column as shown above. A small bleed stream of 0.9 lb/hr (0.4 kg/hr) is removed from the bottom of the APRC. Operating conditions are further summarized in the following table.

| Flow | Units | CPC | HEC | APRC |
|---|---|---|---|---|
| Feed from CKC Bottoms | kg/hr (lb/hr) | 9.5 (21) | — | — |
| Total Feed | kg/hr (lb/hr) | 45 (100) | 17 (38) | 12.7 (28) |
| Reflux | kg/hr (lb/hr) | 36.7 (81) | 29 (64) | 11 (25) |
| Overhead | kg/hr (lb/hr) | 36 (80) | 12.7 (28) | 4 (9) |
| Bottoms | kg/hr (lb/hr) | 17 (38) | 4.5 (10) | 8.6 (19) |
| Bleed (bottoms) | kg/hr (lb/hr) | | | 0.4 (0.9) |
| Overhead Pressure | kPa (psia) | 7 (15.7) | 0.9 (2) | 0.45 (1) |
| Bottoms Pressure | kPa (psia) | 9.3 (20.6) | 1.1 (2.5) | 0.7 (1.5) |
| Overhead Temperature | ° C. | 184 | 100 | 116 |
| Bottoms Temperature | ° C. | 225 | 212 | 130 |
| Phenol in Overhead | wt. % | 99.9 | 9.8 | 0.4 |
| Phenol in Bottoms | wt. % | 7.2 | 0.3 | 14.2 |
| AP in Overhead | wt. % | 0.001 | 88.6 | 98 |
| AP in Bottoms | wt. % | 65.4 | 4 | 84.3 |

The foregoing demonstrates that substantially all of the phenol is predicted to be present in the overhead of the CPC and HEC and in the bottoms of the APRC. The foregoing also demonstrates that substantially all of the AP is predicted to be present in the bottoms of the CPC and in the overhead of the HEC. Some of the AP is predicted to be present in the bottoms of the APRC along with a majority of the phenol, but a majority of the AP and almost none of the phenol is predicted to be present in the overhead of the APRC.

Persons of ordinary skill in the art will recognize that many modifications may be made to the embodiments described herein. The embodiments described herein are meant to be illustrative only and should not be taken as limiting the invention, which will be defined in the claims.

The invention claimed is:

1. A method for producing acetophenone comprising:
    treating one or more alkylbenzenes comprising s-butylbenzene to produce a feed comprising phenol and acetophenone;
    separating a crude phenol stream from the feed under crude phenol separation conditions effective to produce crude phenol heavies, the crude phenol separation conditions comprising a crude phenol operating pressure of from about 70 kPa to about 200 kPa;
    separating an acetophenone stream, comprising acetophenone, acetophenone-phenol azeotrope, and other impurities, directly from the crude phenol heavies under azeotropic distillation conditions, the azeotropic distillation conditions comprising an azeotropic distillation operating pressure of from about 1 to about 30 kPa; and
    separating a refined acetophenone stream from the acetophenone stream under azeotropic distillation conditions effective to leave acetophenone heavies, the azeotropic distillation conditions comprising an azeotropic distillation operating pressure of from about 1 to about 30 kPa.

2. The method of claim 1 further comprising recycling at least a portion of the refined acetophenone heavies to or upstream of the separation of the crude phenol stream from the feed.

3. The method of claim 2 wherein the crude phenol separation conditions and the azeotropic distillation conditions comprise operating temperatures sufficiently high to separate the crude phenol stream and the acetophenone stream, but sufficiently low to minimize dimerization of AP.

4. The method of claim 1 wherein:
    the crude phenol separation conditions comprise a crude phenol operating temperature of 250° C. or less; and
    the azeotropic distillation conditions comprise an azeotropic distillation operating temperature of 230° C. or less.

5. The method of claim 1 further comprising
    recovering about 95 wt. % or more of the AP in the crude phenol heavies in the AP stream; and
    recovering about 90 wt. % or more of the phenol present in the crude phenol heavies.

* * * * *